(12) United States Patent
Narita et al.

(10) Patent No.: US 7,918,918 B2
(45) Date of Patent: Apr. 5, 2011

(54) EXTRACTANTS FOR PALLADIUM AND METHOD OF RAPIDLY SEPARATING AND RECOVERING PALLADIUM USING THE SAME

(75) Inventors: Hirokazu Narita, Tsukuba (JP); Mikiya Tanaka, Tsukuba (JP); Ken Tamura, Tsukuba (JP)

(73) Assignee: National Institute of Advanced Industrial Science & Technology, Tokyo (JP)

( * ) Notice: Subject to any disclaimer, the term of this patent is extended or adjusted under 35 U.S.C. 154(b) by 100 days.

(21) Appl. No.: 12/318,824

(22) Filed: Jan. 9, 2009

(65) Prior Publication Data

US 2009/0178513 A1    Jul. 16, 2009

(30) Foreign Application Priority Data

Jan. 15, 2008  (JP) ................................. 2008-005472
Aug. 5, 2008   (JP) ................................. 2008-201607

(51) Int. Cl.
*C22B 11/00*  (2006.01)
*C01G 55/00*  (2006.01)
*C07C 323/41* (2006.01)

(52) U.S. Cl. ............ 75/741; 423/22; 564/123; 564/192; 568/38; 568/39; 568/44

(58) Field of Classification Search .................... 75/741; 423/22; 564/123, 192; 568/38, 39, 44
See application file for complete search history.

(56) References Cited

U.S. PATENT DOCUMENTS

2007/0172404 A1 *  7/2007  Narita et al. .................... 423/22

FOREIGN PATENT DOCUMENTS

JP   S63-014824   1/1988
(Continued)

OTHER PUBLICATIONS

Narita et al., Solvent extraction of platinum group metals using amide compounds—Palladium extraction with N,N,N',N'-tetra-n-octyl-thiodiglycolamide, Presented at Precios Metals '07 in Brisbane, Australia, Aug. 30-31, 2007.*

*Primary Examiner* — Jerry Lorengo
*Assistant Examiner* — Jared Wood
(74) *Attorney, Agent, or Firm* — Manabu Kanesaka

(57) ABSTRACT

Provided is a novel extractant for palladium capable of improving an extraction rate compared to the conventional extractant, DHS, and also capable of back-extracting palladium using an ammonia solution, and a method of separating and recovering palladium using the novel extractant. The present invention provides a method for obtaining an aqueous solution containing palladium only by: bringing an acidic aqueous solution containing at least palladium into contact with an organic solution containing a sulfide-containing monoamide as an active integredient represented by the following structural formula (I),

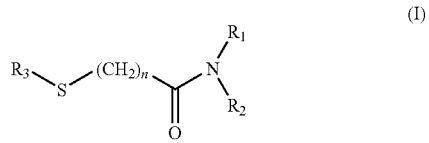

where $R_1$, $R_2$, and $R_3$ each represent a group selected from a chain hydrocarbon group having 1 to 18 carbon atoms which may be branched, an alicyclic hydrocarbon group having 1 to 10 carbon atoms, and an aromatic hydrocarbon group having 1 to 14 carbon atoms, and n represents an integer of 1 to 4; extracting palladium into the organic solution; and conducting the back-extraction of the palladium extracted in the organic solution to an aqueous solution using an ammonia solution.

4 Claims, 4 Drawing Sheets

FOREIGN PATENT DOCUMENTS

| | | |
|---|---|---|
| JP | H03-022402 | 1/1991 |
| JP | H07-310129 | 11/1995 |
| JP | H08-158088 | 6/1996 |
| JP | H08-209259 | 8/1996 |
| JP | H09-279264 | 10/1997 |
| JP | H10-102156 | 4/1998 |
| JP | 2001-107156 | 4/2001 |
| JP | 2004-332041 | 11/2004 |
| WO | WO 2005/083131 | 9/2005 |

* cited by examiner

EXTRACTANTS FOR PALLADIUM AND METHOD OF RAPIDLY SEPARATING AND RECOVERING PALLADIUM USING THE SAME

BACKGROUND OF THE INVENTION

1. Field of the Invention

The present invention relates to extractants for palladium and a method of separating and recovering palladium. In particular, the present invention relates to extractants which can rapidly extract palladium and can back-extract palladium using an ammonia solution, and to a method of separating and recovering palladium using the extractants.

2. Description of the Related Art

In recent years, the demand for autocatalysts has been enhanced worldwide with the tightening of regulations regarding the emissions from automobiles. Since the autocatalysts contain a significant amount of platinum group metals, like palladium, platinum, and rhodium, the improvement of the separation and purification of the metals from their wastes, along with metal refining from ores, has become important, in order to ensure stable supply of those platinum group metals.

For separation and purification of the platinum group metals in practical processes, various methods such as a sedimentation separation method (JP 10-102156 A), an ion exchange method (JP 03-22402 A and JP 07-310129 A), an electrolytic precipitation method (JP 08-158088 A), and a solvent extraction method have been conventionally proposed and carried-out. Of those methods, the solvent extraction method has been widely adopted in view of economy and operability.

For the separation of palladium by the solvent extraction method, it is required that a selective separation of palladium over platinum and rhodium, and over base metals when possible. Di-n-hexylsulfide (DHS) is one of the most commonly used industrial extractants for palladium (JP 08-209259 A, JP 09-279264 A, JP 2001-107156 A, JP-2004-332041 A, and JP 63-14824 A). DHS is capable of selectively extracting palladium from an acidic aqueous solution containing palladium, platinum, and rhodium, and then palladium can be recovered from the DHS solution containing palladium using an ammonia solution. However, the extraction rate of palladium is small when DHS is used alone; therefore, the addition of another extractant to DHS is required to improve the extraction rate (JP 63-14824 A).

Sulfur-containing diamides have been proposed as palladium extractants which can rapidly extract palladium with a high selectivity (WO 2005/083131), but it is difficult to back-extract palladium using an ammonia solution, and the back-extraction requires the use of a hydrochloric acid solution containing thiourea. The use of the hydrochloric acid solution containing thiourea is not necessarily suitable for practical application; therefore, the back-extraction using an ammonia solution is needed.

SUMMARY OF THE INVENTION

The present invention has been carried out in view of the circumstances described above, and an object of the present invention is to provide: a novel extractant for palladium which can extract palladium much faster than DHS, which is one of the most commonly used industrial extractants for palladium, and can easily back-extract palladium using an ammonia solution, unlike the sulfur-containing diamides; and a method of separating and recovering palladium using the novel extractant.

The inventors of the present invention have intensively studied to achieve the above object, and have found that: when a sulfide-containing monoamide is used as the extractant instead of DHS or the sulfur-containing diamide and the extractant is contacted with an acidic aqueous solution containing palladium, a quantitative extraction of palladium can be performed much more rapidly than that using DHS; and, the back-extraction of palladium using an ammonia solution can be easily performed in the sulfide-containing monoamide system, but not in the sulfur-containing diamide system.

The present invention has been accomplished based on those findings, and the present invention provides:

(1) an extractant for palladium including a sulfide-containing monoamide, as an active ingredient, represented by the following general formula (I),

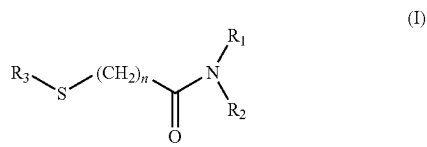

where $R_1$, $R_2$, and $R_3$ each represents a group selected from a chain hydrocarbon group having 1 to 18 carbon atoms which may be branched, an alicyclic hydrocarbon group having 1 to 10 carbon atoms, and an aromatic hydrocarbon group having 1 to 14 carbon atoms, and n represents an integer of 1 to 4;

(2) a method of separating palladium, which includes bringing an acidic aqueous solution containing palladium into contact with an organic solution containing the extractant for palladium according to the item (1) above, thereby extracting palladium in the organic solution;

(3) a method of recovering palladium, which includes subjecting the palladium extracted in the organic solution according to the item (2) above to back-extraction by bringing an ammonia solution into contact with the organic solution, thereby obtaining an aqueous solution containing palladium;

(4) a method of separating and recovering palladium from an acidic aqueous solution containing at least palladium, including: a first step of contacting an acidic aqueous solution containing at least palladium with an organic solution containing the extractant for palladium according to the item (1), to thereby separate palladium from the acidic solution containing at least palladium; and a second step of contacting the obtained organic solution containing palladium with an ammonia solution to thereby recover palladium.

According to the present invention, it is possible, by employing a sulfide-containing monoamide as an extractant for palladium, to extract palladium within a short time, to achieve the separation of palladium from other platinum group metals and base metals, and further, to back-extract palladium using an ammonia solution.

DETAILED DESCRIPTION OF THE INVENTION

Figure 1:
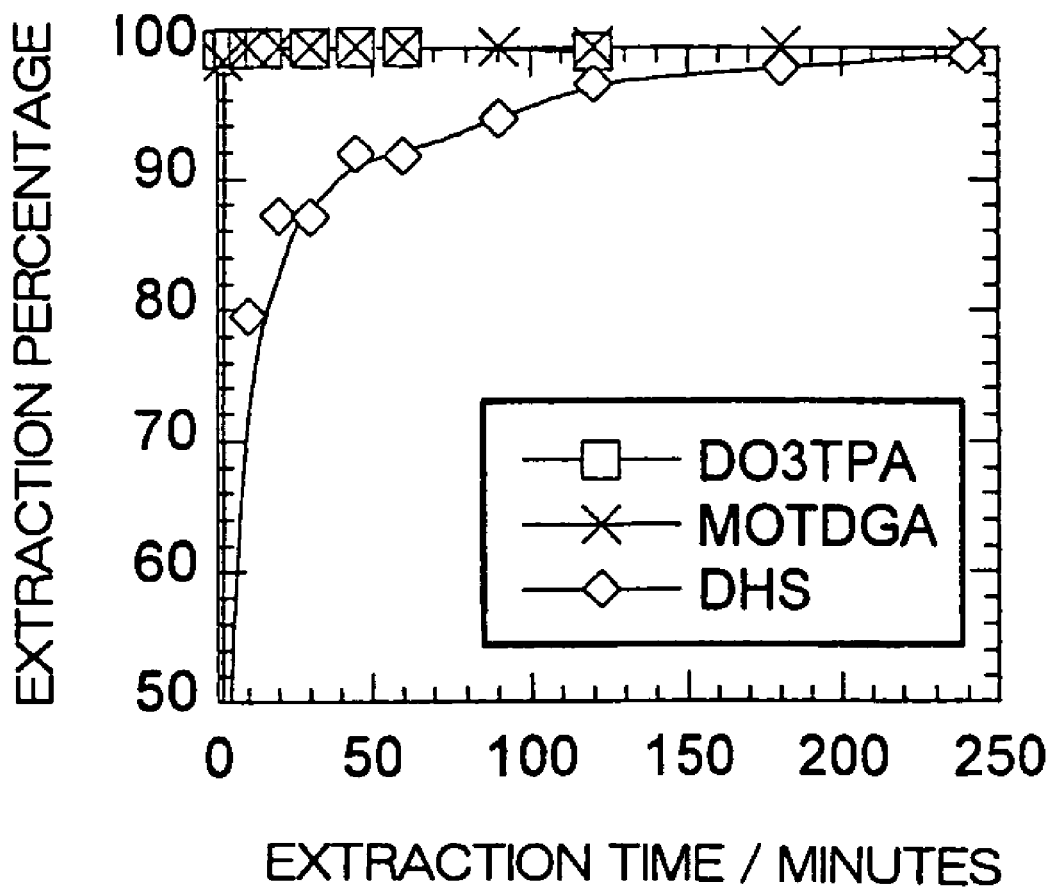
FIG. 1 is a graph showing the extraction percentage of palladium with DO3TPA and DHS as a function of extraction time.

In the present invention, a sulfide-containing monoamide represented by the following general formula (I) is used as an extractant for palladium,

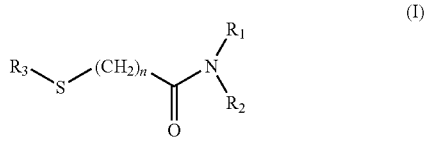

(I)

where $R_1$, $R_2$, and $R_3$ each represents a group selected from a chain hydrocarbon group having 1 to 18 carbon atoms which may be branched, an alicyclic hydrocarbon group having 1 to 10 carbon atoms, and an aromatic hydrocarbon group having 1 to 14 carbon atoms, and n represents an integer of 1 to 4.

Examples of the chain hydrocarbon group having 1 to 18 carbon atoms which may be branched include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, isopropyl, isobutyl, s-butyl, t-butyl, isopentyl, neopentyl, t-pentyl, 2-ethylhexyl, vinyl, allyl, 1-propenyl, isopropenyl, 1-butenyl, 2-butenyl, 2-methylallyl, 1-heptinyl, 1-hexenyl, 1-heptenyl, 1-octenyl, and 2-methyl-1-propenyl groups. Examples of the alicyclic hydrocarbon group having 1 to 10 carbon atoms include cyclobutyl, cyclopentyl, cyclohexyl, cycloheptyl, cyclooctyl, cyclononyl, cyclodecyl, cyclohexenyl, cyclohexadienyl, cyclohexatrienyl, cyclooctenyl, and cyclooctadienyl groups. Examples of the aromatic hydrocarbon group having 1 to 14 carbon atoms include phenyl, naphthyl, anthryl, tolyl, xylyl, cumenyl, benzyl, phenethyl, styryl, cinnaimyl, biphenylyl, and phenanthryl groups.

Specific examples of the sulfide-containing monoamide includes N,N-di-n-octyl-3-thiapentanamide ($R_1$=$R_2$=n-$C_8H_{17}$, $R_3$=$C_2H_5$, n=1), N-methyl-N-n-octyl-3-thiapentanamide ($R_1$=$CH_3$, $R_2$=n-$C_8H_{17}$, $R_3$=$C_2H_5$, n=1), N-methyl-N-n-octyl-4-thiapentanamide ($R_1$=$CH_3$, $R_2$=n-$C_8H_{17}$, $R_3$=$CH_3$, n=2), and N-methyl-N-n-octyl-phenyl-3-thiapentanamide ($R_1$=$CH_3$, $R_2$=n-$C_8H_{17}$, $R_3$=$C_6H_5$, n=1).

These substances are obtained by the reaction of an acid chloride such as ethylthioacetyl chloride with a secondary amine such as dialkylamine.

In order to separate and recover palladium from an acidic aqueous solution containing palladium using the sulfide-containing monoamide represented by the general formula (I) according to the present invention, an extraction solution containing the extractant needs to be prepared in advance, and the extraction solution can be prepared by dissolving the extractant into a hydrophobic organic solvent, e.g., an aliphatic hydrocarbon such as n-dodecane, an alcohol such as 2-ethyl-1-hexanol, an aliphatic chloride such as chloroform, and an aromatic hydrocarbon such as benzene.

Further, a solution to be treated used for a method of separating and recovering palladium using the extractant for palladium may be hydrochloric acid, nitric acid, or the like, in which at least palladium is contained. The solution to be treated may also contain, other than palladium, platinum group metals such as rhodium and platinum and base metals such as iron and copper.

The molar concentration of the sulfide-containing monoamide represented by the general formula (I) contained in the extraction solution is adjusted to have twice or more the molar concentration of palladium contained in the acidic aqueous solution to be treated.

In the solution to be treated, platinum group metals such as rhodium and platinum and base metals such as iron and copper are contained depending on a target substance to be treated, but a selectivity of palladium may decrease when the concentration of the extractant or the acid concentration of the solution to be treated is excessively high.

In the method of separating and recovering palladium of the present invention, first, the acidic aqueous solution to be treated containing at least palladium and an organic solution containing the sulfide-containing monoamide are contacted with each other. The palladium in the acidic solution is extracted into the organic solution immediately, but other platinum group metals such as platinum and rhodium and base metals are hardly extracted and are remained in the aqueous solution.

Next, the palladium that is separated into the organic solution by the above operation can be recovered as an aqueous solution by contact with an ammonia solution.

EXAMPLES

Hereinafter, the features of the present invention are described more specifically by way of examples, but the present invention is not limited to those examples.

Example 1

In this example, the organic syntheses of the sulfide-containing monoamides are described.

(A) N,N-di-n-octyl-3-thiapentanamide (DO3TPA): Ethylthioacetic acid was converted to ethylthioacetic chloride by refluxing a solution of ethylthioacetic acid dissolved in thionyl chloride with a small amount of N,N-dimethylformamide for 1 hours at 50° C. After removing the thionyl chloride, the crude ethylthioacetic chloride remained. The crude extract was dropwise added to a mixed solution of triethylamine and N,N-dioctylamine in chloroform at 10° C. The resulting solution was then refluxed with stirring for 3 hours at 60° C. After cooling to room temperature, the organic solution was successively washed with water, 1 M HCl and a 5% aqueous sodium carbonate solution. The organic phase was next dried over anhydrous sodium sulfate and then concentrated in vacuo. The residue was purified by column chromatography (elution with 19:1 n-hexane:ethylacetate). Found: C, 69.68%; H, 11.75%; N, 4.17%; S, 9.71%. Calcd for $C_{20}H_{41}NOS$: C, 69.89%; H, 12.05%; N, 4.08%; S, 9.33%. $^1H$ NMR ($CDCl_3$): δ 0.87 (6H, —$NC_7H_{14}CH_3$), 1.20-1.37 (3H, -$SCH_2\underline{CH_3}$; 20H, —$NC_2H_4C_5\underline{H_{10}}CH_3$), 1.55 (4H, -$NCH_2\underline{CH_2}$—), 2.68 (2H, -$\underline{SCH_2}CH_3$), 3.24-3.31 (2H, —$\underline{SCH_2}CON$—; 4H, —$N\underline{CH_2}CH_2$—).

IR ($\overline{neat}, vcm^{-1}$): 1641 (C=O).

(B) N-methyl-N-n-octyl-3-thiapentanamide (MO3TPA): Ethylthioacetic acid was converted to ethylthioacetic chloride by refluxing a solution of ethylthioacetic acid dissolved in thionyl chloride with a small amount of N,N-dimethylformamide for 1 hours at 50° C. After removing the thionyl chloride, the crude ethylthioacetic chloride remained. The crude extract was dropwise added to a mixed solution of triethylamine and N,N-methyloctylamine in chloroform at 10° C. The resulting solution was then refluxed with stirring for 2.5 hours at 60° C. After cooling to room temperature, the organic solution was successively washed with water, 1 M HCl and a 5% aqueous sodium carbonate solution. The organic phase was next dried over anhydrous sodium sulfate and then concentrated in vacuo. The residue was purified by column chromatography (elution with 19:1 n-hexane:ethylacetate). Found: C, 63.35%; H, 10.60%; N, 5.73%; S, 13.47%. Calcd for $C_{13}H_{27}NOS$: C, 63.62%; H, 11.09%; N, 5.71%; S, 13.07%. $^1H$ NMR ($CDCl_3$): δ 0.89 (3H, —$NC_7H_{14}CH_3$), 1.20-1.37 (3H, —$SCH_2CH_3$); 10H, —$NC_2H_4C_5H_{10}CH_3$), 1.45-1.67 (2H, —$NCH_2CH_2$—), 2.68 (2H, —$SCH_2CH_3$), 2.94&3.06(3H, —$NCH_3$), 3.28-3.43 (2H, —$SCH_2CON$—; 2H, —$NCH_2CH_2$—).

IR (neat,vcm$^{-1}$): 1644 (C=O).

(C) N-methyl-N-n-octyl-4-thiapentanamide (MO4TPA): 3-methylthiopropionic acid was converted to 3-methylthiopropionic chloride by refluxing a solution of 3-methylthiopropionic acid dissolved in thionyl chloride with a small amount of N,N-dimethylformamide for 1 hours at 50° C. After removing the thionyl chloride, the crude 3-methylthiopropionic chloride remained. The crude extract was dropwise added to a mixed solution of triethylamine and N,N-methyloctylamine in chloroform at 10° C. The resulting solution was then refluxed with stirring for 2 hours at 60° C. After cooling to room temperature, the organic solution was successively washed with water, 1 M HCl and a 5% aqueous sodium carbonate solution. The organic phase was next dried over anhydrous sodium sulfate and then concentrated in vacuo. The residue was purified by column chromatography (elution with 49:1 n-hexane:ethylacetate). Found: C, 63.39%; H, 10.91%; N, 5.81%; S, 13.18% Calcd for $C_{13}H_{27}NOS$: C, 63.62%; H, 11.09%; N, 5.71%; S, 13.07%. $^1H$ NMR ($CDCl_3$): δ 0.89 (3H, —$NC_7H_{14}CH_3$), 1.17-1.38 (10H, —$NC_2H_4C_5H_{10}CH_3$), 1.47-1.62 (2H, —$NCH_2CH_2$—), 2.14 (3H, —$SCH_3$), 2.58-2.64 (2H, —$SCH_2CH_2CON$—), 2.79-2.85 (2H, —$SCH_2CH_2$—), 2.92&2.99 (—$NCH_3$), 3.27&3.36 (2H, —$NCH_2CH_2$—).

IR (neat,vcm$^{-1}$): 1651 (C=O).

(D) N-methyl-N-n-octyl-phenyl-3-thiapentanamide (MOPh3TPA): Benzylthioacetic acid was converted to benzylthioacetic chloride by refluxing a solution of benzylthioacetic acid dissolved in thionyl chloride with a small amount of N,N-dimethylforrnamide for 1 hours at 50° C. After removing the thionyl chloride, the crude benzylthioacetic chloride remained. The crude extract was dropwise added to a mixed solution of triethylamine and N,N-methyloctylamine in chloroform at 10° C. The resulting solution was then refluxed with stirring for 2 hours at 60° C. After cooling to room temperature, the organic solution was successively washed with water, 1 M HCl and a 5% aqueous sodium carbonate solution. The organic phase was next dried over anhydrous sodium sulfate and then concentrated in vacuo. The residue was purified by column chromatography (elution with 97:3 n-hexane:ethylacetate). Found: C, 70.16%; H, 9.68%; N, 4.52%; S, 10.34%. Calcd for $C_{18}H_{29}NOS$: C, 70.31%; H, 9.51%; N, 4.56%; S, 10.43%. $^1H$ NMR ($CDCl_3$): δ 0.89 (3H, —$NC_7H_{14}CH_3$), 1.18-1.32 (10H, —$NC_2H_4C_5H_{10}CH_3$) 1.48-1.60 (2H, —$NCH_2CH_2$—), 2.91&2.96 (—$NCH_3$), 3.13-3.40 (2H, —$SCH_2CON$—; 2H, —$NCH_2CH_2$—), 3.80-3.87 (2H, —$SCH_2C_6H_5$), 7.20-7.43 (—$C_6H_5$).

IR (neat,vcm$^{-1}$): 1643 (C=O).

Example 2

In this example, N,N-di-n-octyl-3-thiapentanamide (DO3TPA), that is a sulfide-containing monoamide of $R_1$=$R_2$=n-$C_8H_{17}$, $R_3$=$C_2H_5$, and n=1 in the above general formula (I), was used as the extractant.

In addition, as known extractants, di-n-hexylsulfide (DHS) and N,N'-dimethyl-N,N'-di-n-octyl-thiodiglycolamide (MOTDGA), which is a sulfur-containing diamide, were used for comparison.

A 0.1 mol/L DO3TPA, DHS or MOTDGA diluted by 80 vol % n-dodecane—20 vol % 2-ethylhexanol and the same volume of 1 mol/L HCl solution containing 0.1 g/L of palladium were vigorously shaken, whereby the palladium was extracted into the organic solution.

The extraction percentages of the metal were determined by measuring the metal concentrations in the aqueous solution before and after the extraction using an ICP emission spectrometer. FIG. 1 shows the extraction percentage of palladium with DO3TPA and DHS as a function of extraction time.

As shown in FIG. 1, using DHS (◊) as the extractant, it takes about 240 minutes to attain almost a 100% palladium extraction, but using MOTDGA (×) or DO3TPA (□), almost a 100% palladium is extracted immediately after the contact of the organic and aqueous solutions.

From the above, it can be concluded that the extraction time of palladium using MOTDGA or DO3TPA is much shorter than that using DHS.

Example 3

In this example, the extraction percentages of palladium, platinum, rhodium, copper, ion, zinc and nickel in a hydrochloric acid solution with DO3TPA were determined as follows.

A 0.1 mol/L DO3TPA diluted by 80 vol % n-dodecane—20 vol % 2-ethylhexanol and the same volume of a hydrochloric acid solution containing 0.1 g/L each of palladium, platinum, rhodium, copper, ion, zinc and nickel were vigorously shaken for 20 minutes, whereby the metals were extracted into the organic solution. The extraction percentages of the metal were determined by measuring the metal concentrations in the aqueous solution before and after the extraction using an ICP emission spectrometer. The results are illustrated in FIG. 2.

Figure 2:
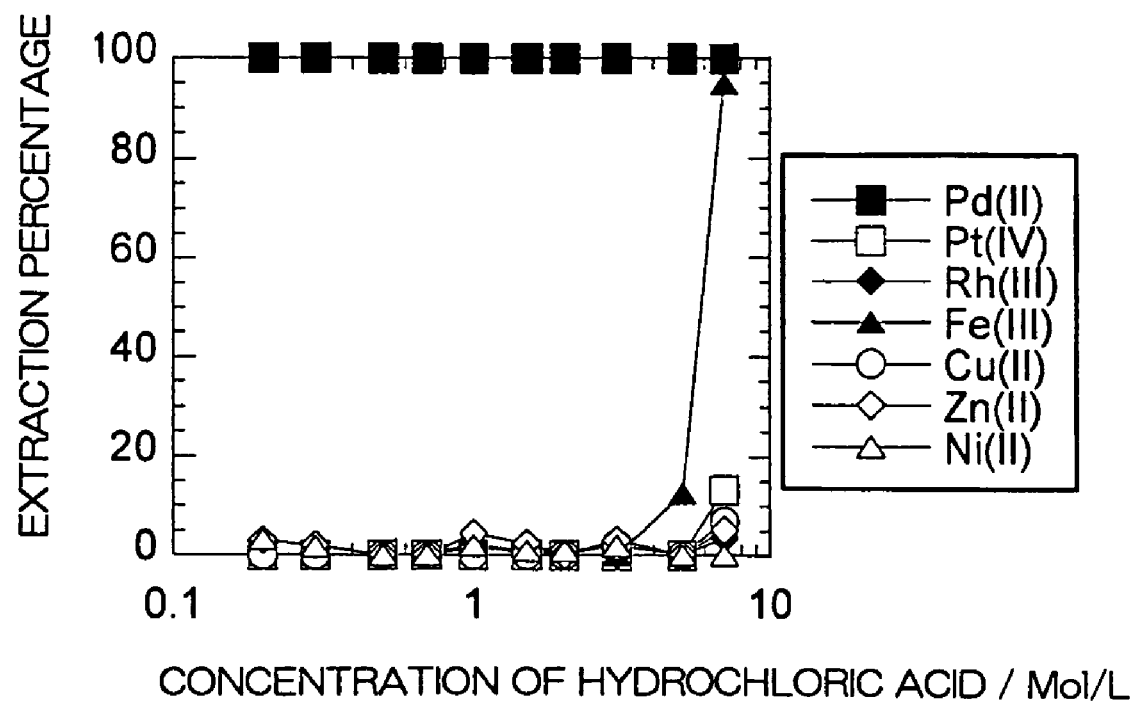
FIG. 2 is a graph showing the extraction percentage of platinum group metals and base metals with DO3TPA as a function of hydrochloric acid concentration.

As illustrated in FIG. 2, it was found that palladium (■) is completely extracted in the organic solution. On the other hand, the other platinum group metals and base metals are hardly extracted in the organic solution when the hydrochloric acid concentration is 5 mol/L or less.

Based on these results, it can be concluded that, by bringing a hydrochloric acid solution containing platinum group metals or base metals into contact with a 0.1 mol/L of DO3TPA diluted by a mixed solvent of 80 vol % of n-dodecane and 20 vol % of 2-ethylhexanol, palladium can be completely and selectively extracted.

In addition, a portion of the organic solution after the palladium extraction from 0.2-7 mol/L hydrochloric acid solution and the same volume of a 28% ammonia solution were shaken for 20 minutes and the metal ions in the organic solution were back-extracted to the aqueous solution. As a result, palladium was back-extracted to the aqueous solution by 80% or more in each case. On the other hand, palladium was hardly back-extracted when MOTDGA was used under the same conditions.

Thus, based on the foregoing results, it can be concluded that palladium can be completely separated from a hydrochloric acid solution in which palladium, platinum, rhodium, and copper, iron, and zinc as base metals are coexistent, by contacting the hydrochloric acid solution with an organic solution containing DO3TPA, and that the palladium extracted in the organic solution can be recovered by contact with an ammonia solution.

Therefore, it can be concluded that using DO3TPA as the extractant, palladium can be selectively extracted in an extremely short time compared to using the conventional extractant, DHS, and the back-extraction of palladium using an ammonia solution can be easily performed unlike that using the sulfur-containing diamides as the extractant.

Example 4

In this example, as the sulfide-containing monoamide represented by the above general formula (I), in addition to the above DO3TPA, N-methyl-N-n-octyl-3-thiapentanamide (MO3TPA: $R_1$=$CH_3$, $R_2$=n-$C_8H_{17}$, $R_3$=$C_2H_5$, n=1), N-methyl-N-n-octyl-4-thiapentanamide (MO4TPA: $R_1$=$CH_3$, $R_2$=n-$C_8H_{17}$, $R_3$=$CH_3$, n=2), and N-methyl-N-n-octyl-phenyl-3-thiapentanamide (MOPh3TPA: $R_1$=$CH_3$, $R_2$=n-$C_8H_{17}$, $R_3$=$C_6H_5$, n=1) were used to examine the effect of the structures of the sulfide-containing monoamides on the extraction time of palladium.

Figure 3:
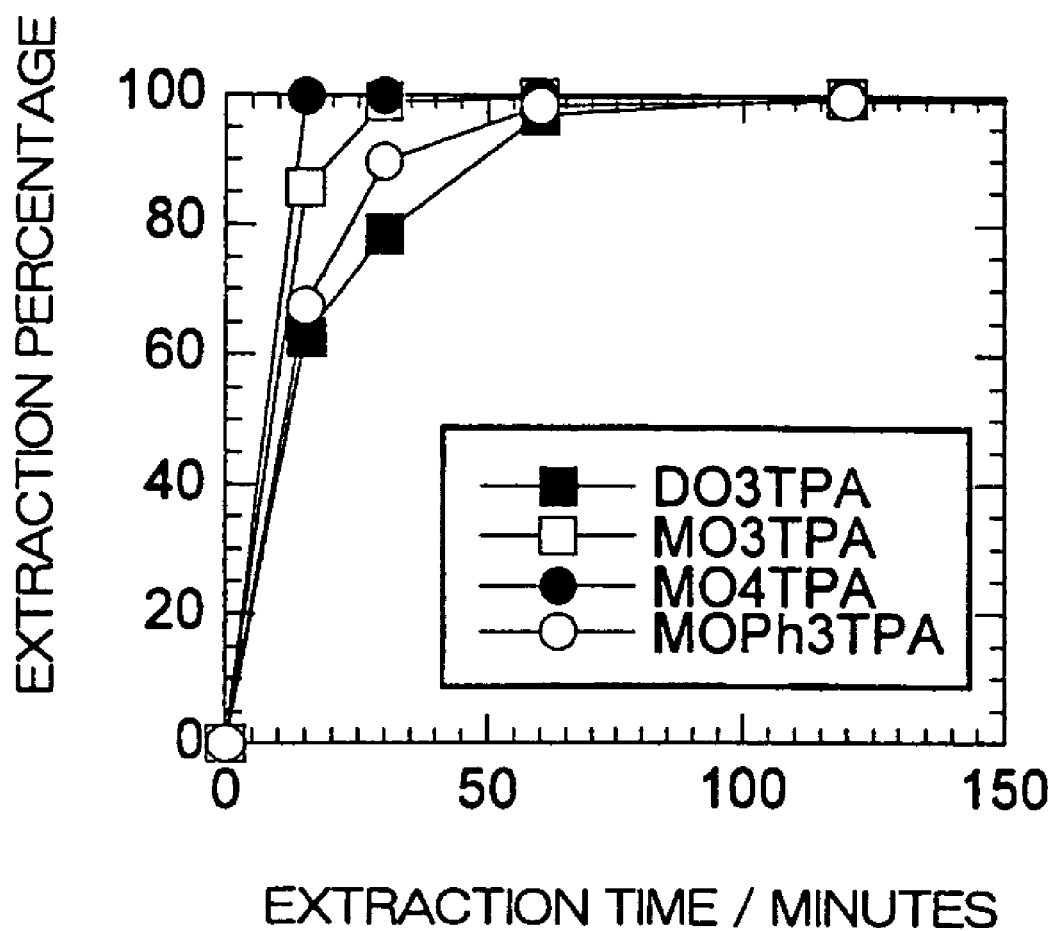
FIG. 3 is a graph showing the extraction percentage of palladium with 4 kinds of sulfide-containing monoamides and DHS as a function of extraction time.

A 0.01 mol/L DO3TPA, MO3TPA, MO4TPA, and MOPh3TPA diluted by 80 vol % n-dodecane—20 vol % 2-ethylhexanol and the same volume of 3 mol/L hydrochloric acid solution containing 0.01 g/L of palladium were vigorously shaken, whereby the palladium was extracted into the organic solution. The extraction percentages of palladium were determined by measuring the metal concentrations in the aqueous solution before and after the extraction using an ICP emission spectrometer. FIG. 3 shows the extraction percentage of palladium with 4 kinds of sulfide-containing monoamides and DHS as a function of extraction time.

As shown in FIG. 3, MO3TPA (□), MO4TPA (●), and MOPh3TPA (○) can extract almost a 100% palladium at the same rate as or more rapidly than DO3TPA (■). Further, each of DO3TPA, MO3TPA, MO4TPA, and MOPh3TPA hardly extracts the other platinum group metals and the base metals under the above conditions, and the extracted palladium can be back-extracted by 80% or more palladium by contacting the organic solution after the extraction of palladium with an equivalent volume of 28% ammonia solution.

Therefore, it can be concluded that extractants including, as an active ingredient, sulfide-containing monoamide such as MO3TPA, MO4TPA, MOPh3TPA, and DO3TPA can cover the defects of the conventional palladium extractants with regard to the extraction rate and back-extraction.

Example 5

In this example, DO3TPA, MO3TPA, MO4TPA, and MOPh3TPA were each used as the sulfide-containing monoamide represented by the general formula (I), and their loading capacity of palladium was determined as follows.

Figure 4:
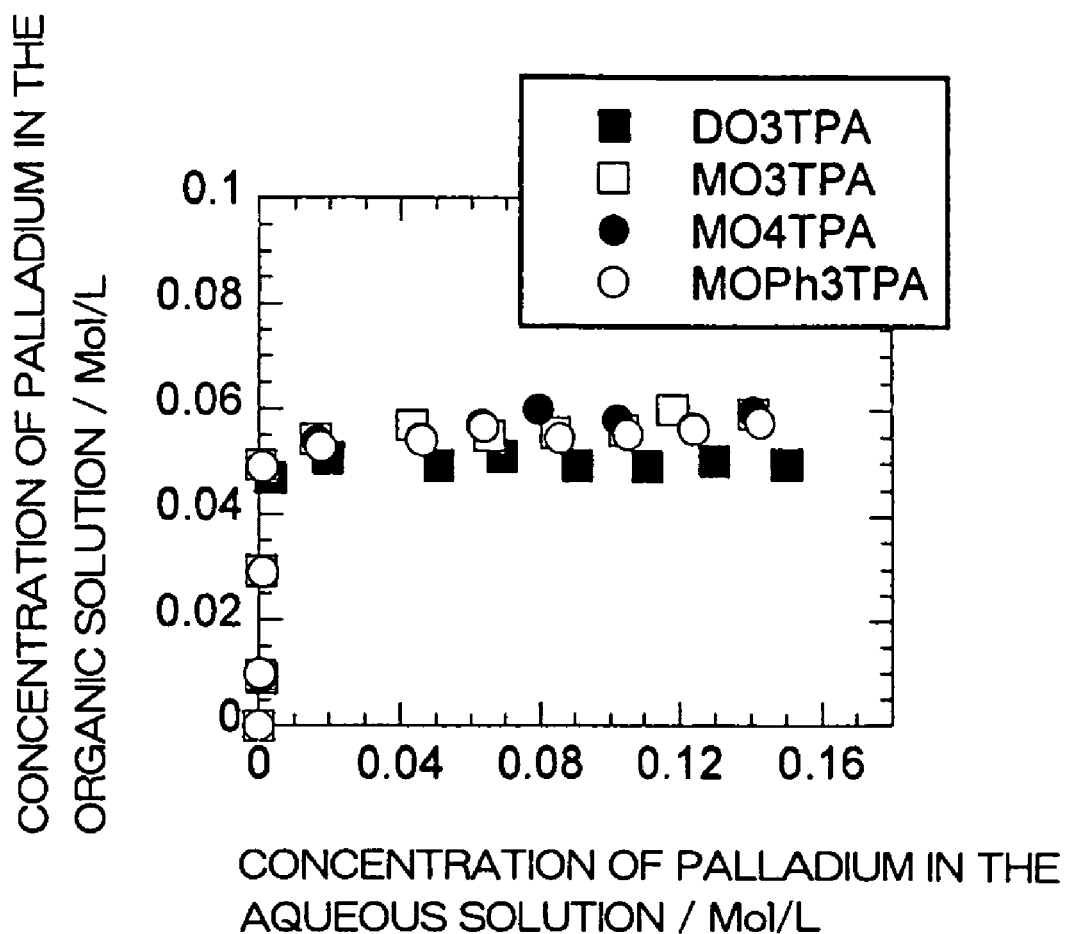
FIG. 4 is a graph showing relationship between the palladium concentrations in the organic and aqueous solutions after extraction equilibrium with 4 kinds of sulfide-containing monoamides.

A 0.1 mol/L DO3TPA, MO3TPA, MO4TPA, and MOPh3TPA diluted by 80 vol % n-dodecane—20 vol % 2-ethylhexanol and the same volume of 3 mol/L hydrochloric acid solution containing palladium were vigorously shaken for 60 minutes, whereby the palladium was extracted into the organic solution. The initial concentration of palladium in the aqueous solution was varied. The concentration of palladium was determined by measuring the metal concentrations in the aqueous solution before and after the extraction using an ICP emission spectrometer. FIG. 4 shows relationship between the palladium concentrations in the organic and aqueous solutions after the extraction equilibrium with 0.1 mol/L DO3TPA, MO3TPA, MO4TPA, and MOPh3TPA.

As shown in FIG. 4, in all the systems, the concentration of saturated palladium in the organic solution (loading capacity) was 0.05 to 0.06 mol/L. This indicates that a 1:2 palladium—sulfide-containing monoamide complex is dominant in the organic solution, which is the same as the palladium—DHS complex (Journal of Chemical Engineering of Japan, Vol. 19, p. 361-366 (1986)). Further, it was also found that quantitative extraction of palladium can be performed using a sulfide-containing monoamide extractant having twice a molar concentration of palladium in the aqueous solution.

What is claimed is:

1. An extractant for palladium including a sulfide-containing monoamide, as an active ingredient, represented by the following general formula (I),

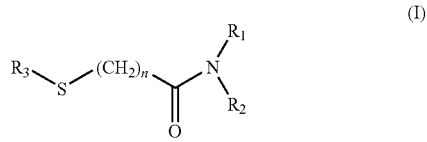

where $R_1$, $R_2$, and $R_3$ each represents a group selected from a chain hydrocarbon group having 1 to 18 carbon atoms which may be branched, an alicyclic hydrocarbon group having 1 to 10 carbon atoms, and an aromatic hydrocarbon group having 1 to 14 carbon atoms, and n represents an integer of 1 to 4.

2. A method of separating palladium, which includes bringing an acidic aqueous solution containing palladium into contact with an organic solution containing the extractant for palladium according to claim 1 above, thereby extracting palladium in the organic solution.

3. A method of recovering palladium, which includes subjecting the palladium extracted in the organic solution according to claim 2 above to back-extraction by bringing an ammonia solution into contact with the organic solution, thereby obtaining an aqueous solution containing palladium.

4. A method of separating and recovering palladium from an acidic aqueous solution to be treated containing at least palladium, comprising:

a first step of contacting the acidic aqueous solution containing at least palladium with an organic solution containing the extractant for palladium according to claim 1, to thereby separate palladium from the acidic aqueous solution to be treated containing at least palladium; and a second step of contacting the obtained organic solution containing palladium with an ammonia solution to thereby recover palladium.

* * * * *